(12) United States Patent
Tuominen et al.

(10) Patent No.: US 8,858,976 B2
(45) Date of Patent: Oct. 14, 2014

(54) IMPLANTABLE PASTE AND ITS USE

(75) Inventors: Jukka Tuominen, Kaarina (FI); Timo Lehtonen, Turku (FI); Fredrik Ollila, Turku (FI)

(73) Assignee: Bonalive Biomaterials Oy, Turku (FI)

( * ) Notice: Subject to any disclaimer, the term of this patent is extended or adjusted under 35 U.S.C. 154(b) by 241 days.

(21) Appl. No.: 13/509,302

(22) PCT Filed: Nov. 12, 2010

(86) PCT No.: PCT/EP2010/067376
§ 371 (c)(1),
(2), (4) Date: Jul. 16, 2012

(87) PCT Pub. No.: WO2011/058134
PCT Pub. Date: May 19, 2011

(65) Prior Publication Data
US 2012/0276164 A1 Nov. 1, 2012

(30) Foreign Application Priority Data
Nov. 12, 2009 (EP) .................................... 09175775

(51) Int. Cl.
| | | |
|---|---|---|
| A61K 35/12 | (2006.01) | |
| A61K 33/40 | (2006.01) | |
| A61K 9/00 | (2006.01) | |
| A61K 31/728 | (2006.01) | |
| A61L 24/00 | (2006.01) | |
| A61K 6/027 | (2006.01) | |
| A61K 6/00 | (2006.01) | |
| A61L 27/46 | (2006.01) | |

(52) U.S. Cl.
CPC ......... *A61L 24/0084* (2013.01); *A61L 2430/02* (2013.01); *A61L 2300/00* (2013.01); *A61K 6/0276* (2013.01); *A61K 6/0008* (2013.01); *A61L 27/46* (2013.01)
USPC .......... 424/422; 424/400; 424/613; 424/93.7; 514/7.6; 514/54; 514/772

(58) Field of Classification Search
USPC ........................................................ 424/400
See application file for complete search history.

(56) References Cited

U.S. PATENT DOCUMENTS

| | | | |
|---|---|---|---|
| 6,190,643 B1 | 2/2001 | Stoor et al. ...................... | 424/49 |
| 2007/0048382 A1 | 3/2007 | Meyer et al. ................... | 424/487 |
| 2008/0226688 A1 | 9/2008 | DePaula ........................ | 424/423 |

FOREIGN PATENT DOCUMENTS

| | | |
|---|---|---|
| EP | 0 408 455 | 1/1991 |
| WO | WO 2007/139760 A2 | 12/2007 |
| WO | WO 2007/139760 A3 | 12/2007 |

*Primary Examiner* — Walter Webb
(74) *Attorney, Agent, or Firm* — James C. Lydon

(57) ABSTRACT

The present invention relates to an implantable paste comprising bioactive glass spheres having a size distribution of 50-425 μm, low molecular weight polyethylene glycol having a molecular weight range of 200-700 g/mol, medium molecular weight polyethylene glycol having a molecular weight range of 700-2500 g/mol and high molecular weight polyethylene glycol having a molecular weight range of 2500-8000 g/mol, with the proviso that the molecular weight of the low molecular weight polyethylene glycol and of the medium molecular weight polyethylene glycol differ from each other by at least 80 g/mol and that the molecular weight of the medium molecular weight polyethylene glycol and of the high molecular weight polyethylene glycol differ from each other by at least 300 g/mol.

10 Claims, No Drawings

IMPLANTABLE PASTE AND ITS USE

The present invention relates to an implantable paste comprising bioactive glass, for surgical uses in mammals.

BACKGROUND OF THE INVENTION

Bioactive glass is a known bioactive and biocompatible material. For decades, bioactive glasses have been investigated as bone filling materials that can bond with bone, even chemically. Recent discoveries of the superior qualities of bioactive glasses have made the materials far more interesting for these applications. Certain bioactive glasses are commercially sold under the trade names of e.g. BonAlive®, Nova-Bone® and Biogran®. Bioactive glasses have been used in different forms for medical applications, such as granules and plates for orthopaedic and cranio-maxillofacial bone cavity filling and bone reconstruction. Certain bioactive glass formulations have been disclosed in the prior art e.g. EP 802 890 and EP 1 405 647. Some compositions of bioactive glasses are also known to have antimicrobial effects e.g. U.S. Pat. No. 6,190,643 and U.S. Pat. No. 6,342,207.

The main benefits of using bioactive glass as a bone graft substitute is that harvesting of the bone grafts from a secondary site can be avoided. Within a certain composition range bioactive glasses stimulate bone growth and show bacterial-growth inhibiting properties.

In order for the glass to be bioactive and have the above-mentioned properties the glass needs to dissolve and to have a certain dissolution rate as well as have certain composition. The relationship between the composition and the bioactivity has been described in Hench L. Bioactive ceramics: Theory and clinical applications. Bioceramics 1994; 7:3-14 in a way that gives a person skilled in the art sufficient tools to design a bioactive glass.

One factor influencing the dissolution rate and therefore the total degradation time of the glass particles is the particle size, or the surface area to volume ratio (A/V). In other words the smaller the particle the higher the A/V ratio and the faster the dissolution and the shorter the total degradation time. For example, the commercially available glass 45S5/Bioglass® is available in a size range from 90-710 μm and it is claimed to dissolve in the body in less than a year. Glass S53P4, sold under the trade name BonAlive®, has a chemical composition of 53 weight-% of $SiO_2$, 23 weight-% of $Na_2O$, 20 weight-% of CaO and 4 weight-% of $P_2O_5$, and it is a clearly slower dissolving glass than the 45S5 glass that has a composition of 45 weight-% of $SiO_2$, 24.5 weight-% of $Na_2O$, 24.5 weight-% of CaO, and 6 weight-% of $P_2O_5$.

In order to enhance the use and to broaden the surgical scope of bioactive glass, mouldable paste or putty types of compositions have been developed. In an ideal case, the putty formulation should be easily dosable, handable and directly administrable to the bone defect without risk of cross-contamination, spillage or excess dosage. In practice, physicians have used their hands in dosing and shaping of putty, and fingers and/or spatula or similar for filling the bone cavities. However, such a formulation possesses a number of practical disadvantages due to e.g. contamination risks during handling, which is not optimal for the patient or the physician.

One synthetic putty/paste formulation is known from US 2008/0226688 and is commercially known as NovaBone® Putty. This document describes a bone void filler type of paste or putty i.e. a sterile formable implant composition for application to a bone defect site comprising bioactive glass particles in an aqueous carrier solution. The bioactive glass particles are added to a viscous carrier at a concentration ranging from about 68% to about 76% (wt/wt). The carrier comprises a mixture of glycerol and polyethylene glycol (PEG) ranging from 24 to 32% (wt/wt) with the ratio of glycerol to polyethylene glycol ranging from about 45:55 to about 65:35.

However, this formulation possesses a number of practical disadvantages; Due to the physical and chemical characteristics and the ratios of the carriers and bioactive glass the material is not easily injectable. In addition, due to the relatively fast resorbing 4555/Bioglass® and the small powder and granule sizes, the formulation is only suitable for fast healing defects and is not suitable for long term bone growth applications. Moreover, the product viscosity is limited to certain applications only and is too high for injectable and syringe usage.

In addition to these disadvantages the risks of accidentally spilling grafting material into soft tissues while trying to reach the bone defect is significantly higher when not having the grafting material in an injectable form. A further disadvantage is that an extra tool e.g. a spatula is needed for the handling.

In addition to fully synthetic bone void filler putties or pastes, certain semi-synthetic mixtures in the form of putty or paste formulations, such as mixtures of allograft bones, demineralised bone matrix and bovine collagen/hydroxyapatite, have been in wide use and are known in the art. In addition, several patent documents on demineralised bone matrix compositions are known e.g. U.S. Pat. No. 5,073,373. Grafton® demineralised bone matrix (DBM) putty and gel bone void filler, bone graft extender and bone graft substitute have been provided for use in surgical bone repair. The composition disclosed in U.S. Pat. No. 5,073,373 is based on a demineralised bone powder in a biocompatible liquid carrier e.g. glycerol. Exactech Resorbable Bone Paste (US 2004/091462 is a mixture of demineralised bone matrix in a bioinert polyethylene glycol (PEG) based polymer and is provided as an aseptic product for single use, as a ready to use implantable device derived from a single donor. The demineralised bone matrix resorbs and is replaced with new bone during the healing process.

However, such allograft formulations possess a number of disadvantages of which the risk of transmission of disease is the largest disadvantage and can never be fully excluded.

DEFINITIONS

The terms used in this application, if not otherwise defined, are those agreed on at the consensus conference on biomaterials in 1987 and 1992, see Williams, D F (ed.): Definitions in biomaterials: Proceedings of a consensus conference of the European Society for Biomaterials, Chester, England. Mar. 3-5, 1986. Elsevier, Amsterdam 1987, and Williams D F, Black J, Doherty P J. Second consensus conference on definitions in biomaterials. In: Doherty P J, Williams R L, Williams D F, Lee A J (eds). Biomaterial-Tissue Interfaces. Amsterdam: Elsevier, 1992.

In this application, by bioactive material is meant a material that has been designed to elicit or modulate biological activity. Bioactive material is often surface-active material that is able to chemically bond with the mammalian tissues.

The term resorbable in this context means that the material is disintegrated, i.e. decomposed, upon prolonged implantation when inserted into mammalian body and when it comes into contact with physiological environment. Especially, the term resorbable glass means silica-rich glass that does not form a hydroxyl-carbonate apatite layer on its surface when in contact with physiological environment. Resorbable glass disappears from the body through resorption and does not significantly activate cells or cell growth during its decomposition process.

By biomaterial is meant a material intended to interface with biological systems to evaluate, treat, augment or replace any tissue, organ or function of the body. By biocompatibility is meant the ability of a material used in a medical device to perform safely and adequately by causing an appropriate host response in a specific location. By resorption is meant decomposition of biomaterial because of simple dissolution. By composite is meant a material comprising at least two different constituents, for example an organic polymer and a ceramic material, such as glass.

OBJECTS AND SUMMARY OF THE INVENTION

An object of the present invention is to provide compositions useful as bone void fillers that are easy and safe to handle and that have the desired properties as to the bone filling effect. Another object of the invention is to overcome the manual handling and moulding problems of clinical use by physicians.

Especially, the present invention aims at providing an injectable paste for the above-mentioned purpose, while still having the desired long term and short term bone growth effects. An additional object of the invention is to provide putty compositions which can be radiation sterilized in a syringe package and have an extended self-life of three years.

The present invention relates to an implantable paste comprising bioactive glass spheres having a size distribution of 50-425 μm, low molecular weight polyethylene glycol having a molecular weight range of 200-700 g/mol, and medium molecular weight polyethylene glycol having a molecular weight range of 700-2500 g/mol.

The invention also relates to the use of a paste according to this invention in manufacturing an implant for use in bone formation.

DETAILED DESCRIPTION OF THE INVENTION

The present invention relates to an implantable paste comprising
 a) bioactive glass spheres having a size distribution of 50-425 μm,
 b) low molecular weight polyethylene glycol having a molecular weight range of 200-700 g/mol,
 c) medium molecular weight polyethylene glycol having a molecular weight range of 700-2500 g/mol and
 d) high molecular weight polyethylene glycol having a molecular weight range of 2500-8000 g/mol,
with the proviso that the molecular weight of the low molecular weight polyethylene glycol and of the medium molecular weight polyethylene glycol differ from each other by at least 80 g/mol and that the molecular weight of the medium molecular weight polyethylene glycol and of the high molecular weight polyethylene glycol differ from each other by at least 300 g/mol.

The present invention thus provides a composition that is osteoconductive, bioactive, injectable and mouldable. The paste comprises bioactive glass spheres and granules in a viscose organic carrier solution or matrix. The paste is thus composed of calcium-phosphorous-sodium-silicate particles mixed with a synthetic binder composed of polyethylene glycol that acts as a temporary binding agent for the particles. The particles and the binder are typically provided as a premixed cohesive material. On implantation, the binder is absorbed to permit tissue infiltration between the particles and permit the normal healing process of bone associated with the particles (resorption of bioactive glass and bone regeneration). Once the binder is absorbed shortly after the implantation, it leaves behind only the bioactive glass particles. The present invention is thus based on an injectable mixture of fully synthetic bioactive glass in a viscous solution based on mixture of low, medium and high molecular weight polyethylene glycols. All of these components are well known and widely used and tolerated in medical, pharmaceutical and cosmetic fields as well as in foods and beverages.

At least part of the above-mentioned objects, if not all, is thus achieved by the present invention and its various embodiments. Indeed, it was surprisingly found that the problems of flow properties of the previous paste formulations can be overcome by using particles with different shapes such as spheres and granules. Additional benefits can be found when varying the particle size distributions of the bioactive glass in two or more fractions. An additional advantage was that the flow properties and use-temperatures can be even more improved by mixing two or more different molecular weight ranges PEGs, optionally together with glycerol.

Moreover, the present paste is indeed injectable, thus avoiding any risk of contamination by contact with the surgeon. It is also easier to fill for example a bond defect, as the paste can be directly injected to the defect, thus filling it gradually and being thus possible to control the even distribution of the paste to the defect.

In the present description, the abbreviation wt-% stands for weight percentage, and is typically expressed as a weight percentage of the total weight. The molecular weight is the mean molecular weight, which is here the number average molecular weight, and is expressed as g/mol. The size distribution of the bioactive glass particles is determined by sieving.

By spheres, it is meant particles that are standard axis-aligned ellipsoid bodies in an xyz-Cartesian three dimensional coordinate system according to equation:

$$\frac{x^2}{a^2} + \frac{y^2}{b^2} + \frac{z^2}{c^2} = 1$$

where a and b are the equatorial radii (along the x and y axes) and c is the polar radius (along the z-axis), all of which are fixed positive real numbers determining the shape of the ellipsoid.

If all three radii are equal, the solid body is a sphere; if two radii are equal, the ellipsoid is a spheroid:
 a=b=c: sphere;
 a=b>c: oblate spheroid (disk-shaped);
 a=b<c: prolate spheroid (like a rugby ball);
 a>b>c: scalene ellipsoid ("three unequal sides").

Also particles that are egg shaped (revolving oval), Archimedean solids (highly symmetric, semi-regular convex polyhedron) excluding solids which have less than 14 faces, and platonic solids (regular convex polyhedron) excluding solids which have less than 12 faces, are included.

By granules, it is meant particles that have any other regular or irregular shape other than above presented.

According to a preferred embodiment, the paste also comprises one of the following
 e) bioactive glass spheres or granules having a size distribution of 500-3000 μm,
 f) glycerol, and/or
 g) therapeutically active agent.

According to a preferred embodiment of the present invention, the bioactive glass portion contains two or more particle size distribution fractions such that one fraction consists of spherical particles. This spherical fraction acts as a lubricant enabling the bioactive glass to flow in an applicator (such as a syringe) without the bridging effect of the granules, which would be otherwise inevitable and lead to high injection pressure and burst effect or jamming of the applicator tube. The spherical particles also enable to use small applicator nozzles for minimal invasive procedures.

In addition, the spherical particles compared to traditional random shaped granules decrease the free volume of the filling of the defect cavity and maximizes the benefits of bioactive glass.

The paste according to the present invention also preferably comprises glycerol.

Polyethylene glycols (PEG), also known as polyethylene oxides, contain the repeating unit (—$CH_2CH_2O$—) and are prepared by stepwise addition of ethylene oxide to a compound containing a reactive hydrogen atom. Polyethylene glycols are prepared by addition of ethylene oxide to ethylene glycol to produce a difunctional polyethylene structure $HO(CH_2CH_2O)_nH$, where n is an integer of varying size depending on the molecular weight of polyethylene glycol.

Polyethylene glycols used in the present invention are generally linear polyethylene glycols i.e. having molecular weight of 100 to 8000 g/mol. Also branched and stars shaped polyethylene glycols can be used to reduce or further tailor the viscosity of the paste. Polyethylene glycols are typically named as PEG with a figure, the figure denoting the mean molecular weight in g/mol. Thus, PEG 400 means polyethylene glycol having mean molecular weight of 400 g/mol and PEG 2000 means polyethylene glycol having mean molecular weight of 2000 g/mol.

Polyethylene glycols (PEGs) are used to form a paste-like material by binding and wetting the bioactive glass particles. In order to achieve suitable viscosity of the paste, at least two PEGs should be mixed together. When choosing the appropriate molecular weights for the PEGs, one should bear in mind that low molecular weight PEG (<600 g/mol) is liquid at room temperature but higher molecular weight PEGs are waxy or solids.

In order to have a paste that remains paste-like in its use temperatures (room and body temperatures), at least three PEGs are mixed together, typically in elevated temperatures. As higher molecular weight PEGs are crystalline materials, their use will raise the upper limit of the use temperature of the paste as well as increase the paste's viscosity and prevent the sedimentation of bioactive glass particles in room temperature during storage. In order to decrease the lower limit of the use temperature, i.e. widening the use temperature range, low molecular weight PEGs are useful for avoiding solidification i.e. hardening of the paste at lower temperatures, as high molecular weight PEGs tend to crystallize in low temperatures.

If only one molecular weight waxy or solid PEG would be used, the use temperature would be too narrow for practical uses. PEG 600 (i.e. polyethylene glycol having 600 g/mol as mean molecular weight) shows a melting range of about 17 to 22° C., so it may be liquid at room temperature but pasty at lower ambient temperatures, while PEGs with 800 to 2000 mean molecular weight are pasty materials with a low melting range. Above a molecular weight of 3000, the polyethylene glycols are typically solids.

Glycerol, i.e. propane-1,2,3-triol, is commonly called glycerin or glycerine. It is a colourless, odourless, viscous liquid that is widely used in pharmaceutical formulations.

Glycerol may be added to the paste to improve its smoothness and to provide further lubrication by enhancing the thermal and viscosity properties due to the physical interactions between PEGs and glycerol. PEGs and glycerol are compatible with each other.

PEG 400 is miscible in all proportions to glycerol but the dissolving power and the solubility of PEGs in glycerol decreases as the molar mass increases. However, both of these properties can be improved by moderate heating and substances that dissolve at room temperature in PEG 400 are soluble to roughly the same extent in molten PEG 4000 (i.e. at a temperature of 60-70° C.).

According to one embodiment of the invention, the total amount of bioactive glass is 50-67 wt-% of the total weight of the paste. Thus, the amount of bioactive glass spheres having a size distribution of 50-425 µm (a) is 10-100 wt-% of the total weight of the bioactive glass and the amount of bioactive glass spheres or granules having a size distribution of 500-3000 µm, (d) is 90-0 wt-% of the total weight of the bioactive glass in the paste.

Preferably, the total amount of polyethylene glycols is 23-50 wt-% of the total weight of the paste, such that amount of low molecular weight PEG (c) is 2-15 wt-% and amount of medium molecular weight PEG (d) is 8-48 wt-% of the total weight of the paste. When high molecular weight PEG is used, its amount is up to 10 wt-% of the total weight of the paste.

In the embodiment where glycerol is used, its amount is up to 10 wt-% of the total weight of the paste. Some suitable pastes have the following composition:

| | |
|---|---|
| PEGs (b + c + d) | 23-45 wt-%, |
| glycerol (f) | 0-10 wt-% and |
| bioactive glass (a + e) | 55-67 wt-%. |

Some preferable pastes have following composition range:

| | |
|---|---|
| low molecular weight PEG (b) | 4-10 wt-% |
| medium molecular weight PEG (c) | 13-18 wt-% |
| High molecular weight PEG (d) | 1-8 wt-% |
| Glycerol (f) | 8-10 wt-% |
| Bioactive glass spheres (a) | 8-12 wt-% |
| Bioactive glass spheres or granules (e) | 48-52 wt-%. |

According to an embodiment of the invention, the amount of therapeutically active agent (h) is up to 40 wt-% of the total weight of the paste. The therapeutically active agent can be selected from the group consisting of growth factors, proteins, peptides, antibiotics, mucopolysaccharides i.e hyaluronic acid, stem cells, peroxides, and mixtures thereof, and be used to promote bone growth or to have an antimicrobial such as antibacterial effect.

In an embodiment of the invention, the composition of the bioactive glass is 53 weight-% of $SiO_2$, 23 weight-% of $Na_2O$, 20 weight-% of CaO and 4 weight-% of $P_2O_5$. Such bioactive glass is sold under the trade name of BonAlive®. This embodiment provides a fast in vivo dissolving binder composition that permits the normal healing process of bone associated with BonAlive® Granules (resorption of bioactive glass and bone regeneration). Due to the slow dissolution rate of BonAlive® bioactive glass chemical composition and particle size the long term bone growth effect will be naturally achieved, but also short term bone growth can be achieved by using significantly smaller particles together with BonAlive® granules.

Pastes comprising all the ingredients at the extreme ends of the ranges may not necessarily give optimal flow and product properties. For example, combining a high molecular weight PEG in high concentration without sufficient low molecular weight PEG and/or glycerol may give high viscose product, which is not suitable for injection at room or body temperatures. A person skilled in the art will however be able to find out the ideal ratio of ingredients through some easy experimentation, for each set of desired properties. Some examples of suitable combinations are also given in the Experimental part below.

The invention also provides a method of producing injectable and mouldable bone void filler paste, which includes melting and mixing the raw materials in controlled conditions, as well as cooling, packaging and conditioning of the final products.

The paste is typically produced by mixing and/or melting the ingredients together in a batch mixer at a temperature of 25 to 95° C. under a protective gas or vacuum or in atmospheric conditions for 5 to 60 min. The mixture is then cooled to 25-45° C. and transferred to applicator and/or stored for further use. Alternatively, the mixing, melting and/or transferring can be done by using any type of mixing equipment e.g. an open or closed batch mixer, continuous stirring tank reactor or mixer, extruder, injection moulding machine, tube reactor or other standard melt processing or melt mixing equipment known in the field.

The invention also provides a use of the present paste in manufacturing an implant for use in bone formation, such as at a bone defect site, i.e. as a bone void filler paste.

In addition, the invention also provides bone growth promoting compositions comprising the above mentioned formulation with active agents. The active agent may be any pharmaceutically active agent for human or animal use.

Different embodiments of the present invention will now be described in more detail in the following Examples. The effects of type, amount and ratios of starting materials, as well as processing and storage conditions can be seen in the Examples, Tables and Figures.

EXPERIMENTAL PART

Generalized Manufacturing Method for Putty:

Glycerol and PEG 400, if used, was added to a heated reactor (60° C.) using 100 RPM (rotations per minute) mixing speed followed by addition of PEG 1500 and PEG 3000, if used. PEGs were supplied by Clariant and glycerol was supplied by Uniqema or Sigma-Aldrich. Low particle size BAG was added to the molten mixture and mixed until the mixture was homogenous and high particle size BAG was added. The mixing continued until the mixture was coherent and pliable. Putty was cooled down to room temperature (RT) under mixing and the vessel was discharged, packed and stored in a desiccator for further use and testing.

Example 1

Comparison of the Properties of Different Putty Compositions

Four compositions that all contained 67% of glass granules and or spheres were prepared. The compositions differed in the proportions of the polyethylene glycols used as shown in Table 1. In this Table, BAG stands for bioactive glass and the diameters of the particles and spheres is given in μm. The total content of glass can be calculated by adding up the amounts of different sizes, the total amount being given in weight percentage. PEG stands for polyethylene glycol and the figure behind denotes the average molecular weight in g/mol. The amounts of PEG's and glycerol are also given in weight-%.

To make a composition both injectable and mouldable, spherical granules together with a low molecular weight polyethylene glycol (here PEG 400) need to be added, which is demonstrated in Composition 4. Indeed, the Compositions 1, 2 and 3 were not injectable. The Composition 3 was mouldable but sticky.

TABLE 1

| Composition | BAG content (wt-%) | PEG 400 (wt-%) | PEG 1500 (wt-%) | PEG 3000 (wt-%) | Glyserol (wt-%) | Injectable | Mouldable |
|---|---|---|---|---|---|---|---|
| Composition 1 | | | | | | | |
| BAG/(μm) Particles | | | 23 | | 10 | No | Yes |
| 500-800 | 40 | | | | | | |
| 315-500 | 13.5 | | | | | | |
| 90-315 Spheres | 13.5 | | | | | | |
| 90-425 | | | | | | | |
| Composition 2 | | | | | | | |
| BAG/(μm) Particleles | | | 17 | 6 | 10 | No | Yes |
| 500-800 | 40 | | | | | | |
| 315-500 | 13.5 | | | | | | |
| 90-315 Spheres | 13.5 | | | | | | |
| 90-425 | | | | | | | |
| Composition 3 | | | | | | | |
| BAG/(μm) | | 8 | 9 | 6 | 10 | No | Yes |

TABLE 1-continued

| Composition | BAG content (wt-%) | PEG 400 (wt-%) | PEG 1500 (wt-%) | PEG 3000 (wt-%) | Glyserol (wt-%) | Injectable | Mouldable |
|---|---|---|---|---|---|---|---|
| Particles | | | | | | | |
| 500-800 | 40 | | | | | | |
| 315-500 | 13.5 | | | | | | |
| 90-315 | 13.5 | | | | | | |
| Spheres | | | | | | | |
| 90-425 | | | | | | | |
| Composition 4 | | | | | | | |
| BAG/(μm) Particles | | 8 | 12 | 3 | 10 | Yes | Yes |
| 500-800 | 40 | | | | | | |
| 315-500 | | | | | | | |
| 90-315 | | | | | | | |
| Spheres | | | | | | | |
| 90-425 | 27 | | | | | | |

Example 2

Injectable Putty Composition Formulation (Nozzle Diameter <2 mm)

A composition was formulated by mixing 120 g of bioactive glass spheres having a particle size of 50-425 μm with carrier made up of 20 g of glycerol and 16 g of PEG 400, 32 g of PEG 1500 and 12 g of PEG 3000 in a laboratory scale stirred tank reactor/mixer according to the above-described generalized manufacturing method for putty. The composition had a total glass percentage of 60% by weight and was flowable through a nozzle diameter of less than 2 mm.

Example 3

Injectable Putty Composition Formulation (Nozzle Diameter <8 mm)

A composition was formulated by mixing 24 g of bioactive glass spheres having a particle size of 50-425 μm and 96 g of bioactive glass particles having a particle size of 500-800 μm with carrier made up of 20 g of glycerol and 16 g of PEG 400, 32 g of PEG 1500 and 12 g of PEG 3000 in a laboratory scale stirred tank reactor/mixer according to the above-described generalized manufacturing method for putty. The composition had a total glass percentage of 60% by weight and was flowable through a nozzle diameter of less than 8 mm.

Example 4

Injectable Putty Composition Formulation (Nozzle Diameter ≤8 mm)

A composition was formulated by mixing 96 g of bioactive glass spheres having a particle size of 90-425 μm and 384 g of bioactive glass particles having a particle size of 500-800 μm with carrier made up of 80 g of glycerol and 72 g of PEG 400, 136 g of PEG 1500 and 32 g of PEG 3000 in a pilot scale stirred tank reactor/mixer according to the above-described generalized manufacturing method for putty. The composition had a total glass percentage of 60% by weight and was flowable through a nozzle diameter of less than 8 mm.

Example 5

Injectable Putty Composition Formulation (Nozzle Diameter ≤8 mm)

A composition was formulated by mixing 96 g of bioactive glass spheres having a particle size of 90-425 μm and 384 g of bioactive glass particles having a particle size of 500-800 μm with carrier made up of 80 g of glycerol and 64 g of PEG 400, 128 g of PEG 1500 and 48 g of PEG 3000 in a pilot scale stirred tank reactor/mixer according to the above-described generalized manufacturing method for putty. The composition had a total glass percentage of 60% by weight and was flowable through a nozzle diameter of less than 8 mm.

The invention claimed is:

1. An implantable paste comprising
   a) bioactive glass spheres having a size distribution of 50-425 μm,
   b) low molecular weight polyethylene glycol having a molecular weight range of 200-700 g/mol, in an amount of 2-15 wt-% of the total weigh of the paste,
   c) medium molecular weight polyethylene glycol having a molecular weight range of 700-2500 g/mol, in an amount of 8-48% of the total weight of the paste, and
   d) high molecular weight polyethylene glycol having a molecular weight range of 2500-8000 g/mol, in an amount of up to 10 wt-% of the total weight of the paste,
with the proviso that the molecular weight of the low molecular weight polyethylene glycol and of the medium molecular weight polyethylene glycol differ from each other by at least 80 g/mol and that the molecular weight of the medium molecular weight polyethylene glycol and of the high molecular weight polyethylene glycol differ from each other by at least 300 g/mol.

2. The paste according to claim 1, further comprising at least one of the following
   e) bioactive glass spheres or granules having a size distribution of 500-3000 μm,
   f) glycerol, and/or
   g) therapeutically active agent.

3. The paste according to claim 2, wherein the amount of bioactive glass spheres having a size distribution of 50-425 μm (a) is 10-100 wt-% of the total weight of the bioactive glass and wherein the amount of bioactive glass spheres or granules having a size distribution of 500-3000 μm (e) is 90-0 wt-% of the total weight of the bioactive glass in the paste.

4. The paste according to claim 1, wherein the total amount of bioactive glass is 50-67 wt-% of the total weight of the paste.

5. The paste according to claim 1, wherein the total amount of polyethylene glycols is 23-50 wt-% of the total weight of the paste.

6. The paste according to claim 1, wherein the amount of high molecular weight polyethylene glycol is up to 10 wt-% of the total weight of the paste.

7. The paste according to claim 1, wherein the amount of glycerol is up to 10 wt-% of the total weight of the paste.

8. The paste according to claim 1, wherein the amount of therapeutically active agent is up to 40 wt-% of the total weight of the paste.

9. The paste according to claim 1, wherein the therapeutically active agent is selected from the group consisting of growth factors, proteins, peptides, antibiotics, mucopolysaccharides, hyaluronic acid, stem cells, peroxides, and mixtures thereof.

10. The paste according to claim 1, wherein the composition of the bioactive glass is 53 weight-% of $SiO_2$, 23 weight-% of $Na_2O$, 20 weight-% of CaO and 4 weight-% of $P_2O_5$.

* * * * *